United States Patent [19]

Leopold

[11] 4,127,674
[45] Nov. 28, 1978

[54] METHOD OF TREATMENT FOR GLAUCOMA

[75] Inventor: Irving H. Leopold, Newport Beach, Calif.

[73] Assignee: Allergan Pharmaceuticals, Inc., Irvine, Calif.

[21] Appl. No.: 779,340

[22] Filed: Mar. 21, 1977

[51] Int. Cl.$^2$ .......................................... A61K 31/165
[52] U.S. Cl. .................................................. 424/324
[58] Field of Search ......................................... 424/324

[56] References Cited

U.S. PATENT DOCUMENTS

| | | | |
|---|---|---|---|
| 3,644,353 | 2/1972 | Lunts et al. | 424/248.56 |
| 3,644,520 | 2/1972 | Hartley et al. | 424/324 |
| 3,705,233 | 12/1972 | Lunts et al. | 424/45 |
| 3,732,300 | 5/1973 | Lunts et al. | 424/324 |
| 3,818,101 | 6/1974 | Baile et al. | 424/324 |
| 3,944,611 | 3/1976 | Smith | 424/324 |
| 4,012,444 | 3/1977 | Lunts et al. | 424/324 |

OTHER PUBLICATIONS

Chem. Abst. 71, 91066(f), (1969) – Lunts et al.
Chem. Abst. 77, 147,680(v), (1972) – Farmer et al.
Chem. Abst. 84, 38912(w), (1976) – Richards et al.

Primary Examiner—Albert T. Meyers
Assistant Examiner—D. W. Robinson
Attorney, Agent, or Firm—Martin A. Voet

[57] ABSTRACT

An ophthalmic composition comprising a compound having the structural formula

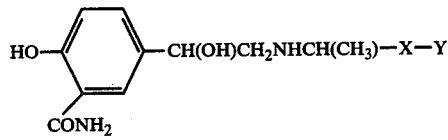

wherein X is selected from the group consisting of $CH_2$—$CH_2$, $CH_2$ and $OCH_2$; and Y is selected from the group consisting of phenyl, P-methoxy phenyl and O-methoxy phenyl and a pharmaceutically acceptable salt thereof and a topically administrable ophthalmic pharmaceutical carrier. The foregoing composition is useful in lowering intraocular pressure in the eye. Reduction of intraocular pressure is of particular importance in the treatment of glaucoma, a disease characterized by elevated intraocular pressure.

3 Claims, No Drawings

METHOD OF TREATMENT FOR GLAUCOMA

BACKGROUND OF THE INVENTION

1. Field of the Invention

The present invention relates to a topical ophthalmic composition and method for the therapeutic use thereof. More particularly, the present invention relates to a topical, opthalmic composition useful in temporarily reducing intraocular pressure and alleviating the symptoms of glaucoma.

2. BACKGROUND OF THE PRIOR ART

The active compounds described herein are known in the art, e.g., German Offen. No. 2,021,445. Labetalol is the designated name for a compound having the structural formula

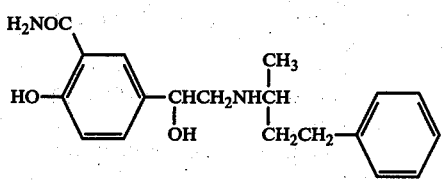

with the chemical name 5-[1-hydroxy-2(1-methyl-3-phenylpropyl) aminoethyl] salicylamide. Its method of manufacture is disclosed in German Offen. No. 2,032,642, the relevant portions of which are hereby incorporated by this reference. Labetalol is known to be a systemic inhibitor of both alpha and beta adrenergic receptors and has been used heretofore in the treatment of systemic hypertension.

Glaucoma is a condition of the eye characterized by increased intraocular pressure. Untreated, the condition eventually leads to irreversible retinal damage and blindness. Conventional therapy for glaucoma is with pilocarpine and/or epinephrine administered topically to the eye several times daily.

SUMMARY OF THE INVENTION

The present invention relates to a therapeutic composition comprising a topically administrable ophthalmic formulation containing an effective amount of a compound selected from the group consisting of a compound having the structural formula

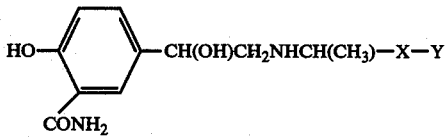

wherein X is selected from the group consisting of $CH_2-CH_2$, $CH_2$ and $OCH_2$; and Y is selected from the group consisting of phenyl, P-methoxy phenyl and O-methoxy phenyl and a pharmaceutically acceptable salt thereof.

The present invention also relates to a method for temporarily reducing intraocular pressure in humans comprising topically administering to the eyes of a human an effective amount of the foregoing composition.

The present invention also relates to a method for temporarily alleviating the symptoms of glucoma in humans comprising topically administering to the eyes of a human having glaucoma an effective amount of the foregoing composition.

DETAILED DESCRIPTION OF THE INVENTION

Many physiologically and pharmaceutically acceptable salts of the compounds discussed above are known to those skilled in the art and all such salts may be employed in the present invention. Examples of suitable acids to form salts with Labetalol include fumaric, hydrochloric, nitric, sulfuric and tartaric acids. The concentration of the active compound which may be used in the present invention ranges from about 0.1 to about 5 percent and preferably from about 0.5 to about 2 percent by weight.

Suitable ophthalmic carriers are known to those skilled in the art and all such conventional carriers may be employed in the present invention. Thus, a particular carrier may take the form of a sterile, ophthalmic ointment, cream, gel, solution, or dispersion. Also including as suitable ophthalmic carriers are slow release polymers, e.g., "Ocusert" polymers, "Hydron" polymers, etc. Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetylpyridium chloride, phenyl mercuric salts, thimerosal, etc., for aqueous formulations, and used in amounts which are non-toxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcelullose, glycerine and EDTA. The solutions are preferably maintained at substantially neutral pH and isotonic with appropriate amounts of conventional buffers, e.g., phosphate, borate, acetate, tris, etc.

A preferred ophthalmic is a preserved aqueous solution containing the following ingredients at the indicated concentration.

| Labetalol | Wt. percent | 1.0 |
|---|---|---|
| Stabilizer | " | 0.01 |
| Preservative | " | 0.005 |
| Buffer | M | 0.05 |
| NaCl q.s. ad isotonic. | | |
| Water q.s. ad 100 percent. | | |

The amount of the foregoing composition to be used in the therapeutic treatment of glaucoma will vary with the age of the patient and the severity of the glaucoma. Generally a dose level of one or two drops of the foregoing aqueous solution 1–4 times daily would be a suitable dosage amount.

EXAMPLE

The intraocular pressure of six albino rabbits was measured tonometrically to obtain a baseline. A 1% isotonic, aqueous solution of Labetalol was prepared and 0.05 ml administered to the right eye of each rabbit. A similar volume of physiologic saline was placed in the left eye. At specified intervals (0, 0.5, 1, 2, 3, 4 and 5 hours after treatment) the intraocular pressure of both eyes of each rabbit was measured tonometrically. The results are shown in Table 1 below.

Table 1

| Rabbit No. | Eye | Intraocular Pressure (mm-Hg) | | | | | | |
|---|---|---|---|---|---|---|---|---|
| | | 0 hr. | 0.5 hr. | 1 hr. | 2 hr. | 3 hr. | 4 hr. | 5 hr |
| 1 | R | 24 | 21 | 21 | 19 | 22 | 23 | 24 |
|   | L | 25 | 24 | 27 | 24 | 24 | 24 | 26 |
| 2 | R | 24 | 17 | 19 | 20 | 21 | 22 | 24 |
|   | L | 24 | 24 | 25 | 21 | 21 | 25 | 22 |
| 3 | R | 28 | 16 | 18 | 19 | 20 | 21 | 22 |
|   | L | 27 | 26 | 26 | 24 | 23 | 22 | 23 |
| 4 | R | 26 | 19 | 19 | 21 | 20 | 19 | 23 |
|   | L | 24 | 22 | 21 | 22 | 20 | 19 | 21 |
| 5 | R | 22 | 18 | 17 | 19 | 24 | 21 | 22 |
|   | L | 22 | 29 | 22 | 22 | 25 | 21 | 22 |
| 6 | R | 27 | 22 | 23 | 21 | 20 | 21 | 24 |
|   | L | 26 | 26 | 26 | 23 | 23 | 24 | 24 |
| MEAN | R | 25 | 19 | 20 | 20 | 21 | 21 | 23 |
|   | L | 25 | 25 | 25 | 23 | 23 | 23 | 23 |
| Mean diff. (R-L) | | +0.5 | −6.0 | −5.0 | −3.0 | −1.5 | −1.0 | 0 |

Conclusions: Treatment of one eye of each six normal albino rabbits with 0.05 ml of a 1% solution of Labetalol resulted in a significant decrease in IOP of the treated eye as compared to the control eye. The peak effect was seen 30 minutes after treatment. Pressure values returned approximately to pretreatment levels within about five hours after treatment.

I claim:

1. A method for treating glaucoma in humans comprising topically applying to the eye of a human having glaucoma an effective, intraocular pressure-reducing amount of 5-[1-hydroxy-2-(1-methyl-3-phenylpropyl)aminoethyl] salicylamide or a pharmaceutically acceptable salt thereof.

2. The method of claim 1 wherein the 5-[1-hydroxy-2-(1-methyl-3-phenylpropyl)aminoethyl] salicylamide or a pharmaceutically acceptable salt thereof is applied in a composition which additionally comprises a topical ophthalmic carrier.

3. The method of claim 2 wherein an effective amount is between about 0.1 and about 5%.

* * * * *